United States Patent [19]
Ehlers

[11] Patent Number: 5,100,419
[45] Date of Patent: Mar. 31, 1992

[54] DEVICE FOR REMOVING DIVERTICULA IN THE COLON

[76] Inventor: Robert L. Ehlers, 414 Rehnberg Pl. 31, West St. Paul, Minn. 55118

[21] Appl. No.: 611,439

[22] Filed: Nov. 13, 1990

Related U.S. Application Data

[63] Continuation of Ser. No. 512,546, Apr. 17, 1990, abandoned, which is a continuation of Ser. No. 215,868, Jul. 6, 1988, abandoned.

[51] Int. Cl.$^5$ .............................................. A61B 17/12
[52] U.S. Cl. .................................................... 606/140
[58] Field of Search ................................. 606/140, 141

[56] References Cited

U.S. PATENT DOCUMENTS

| | | | |
|---|---|---|---|
| 3,545,444 | 12/1970 | Green | 128/326 X |
| 3,643,653 | 2/1972 | Takahashi et al. | |
| 3,870,048 | 3/1975 | Yoon | |
| 3,911,923 | 10/1975 | Yoon | 128/303 A |
| 3,967,625 | 7/1976 | Yoon | |
| 3,985,138 | 10/1976 | Jarvik | 128/326 |
| 3,989,049 | 11/1976 | Yoon | |
| 4,038,988 | 8/1977 | Perisse | 128/326 |
| 4,085,743 | 4/1978 | Yoon | |
| 4,103,680 | 8/1978 | Yoon | |
| 4,257,419 | 3/1981 | Goltner et al. | 128/303 A |
| 4,257,420 | 3/1981 | Terayama | |
| 4,374,517 | 2/1983 | Hagiwara | |
| 4,374,523 | 2/1983 | Yoon | |
| 4,493,319 | 1/1985 | Polk et al. | |
| 4,735,194 | 4/1988 | Stiegmann | 128/303 A X |

Primary Examiner—Michael H. Thaler
Attorney, Agent, or Firm—Merchant, Gould, Smith, Edell, Welter & Schmidt

[57] ABSTRACT

The present invention is a medical device for inverting diverticulum and closing such diverticulum in the inverted position. The apparatus includes a reciprocating vacuum tube for inverting the diverticulum and a caliper for placing a fastening device such as an elastic band around the base of the diverticulum.

10 Claims, 5 Drawing Sheets

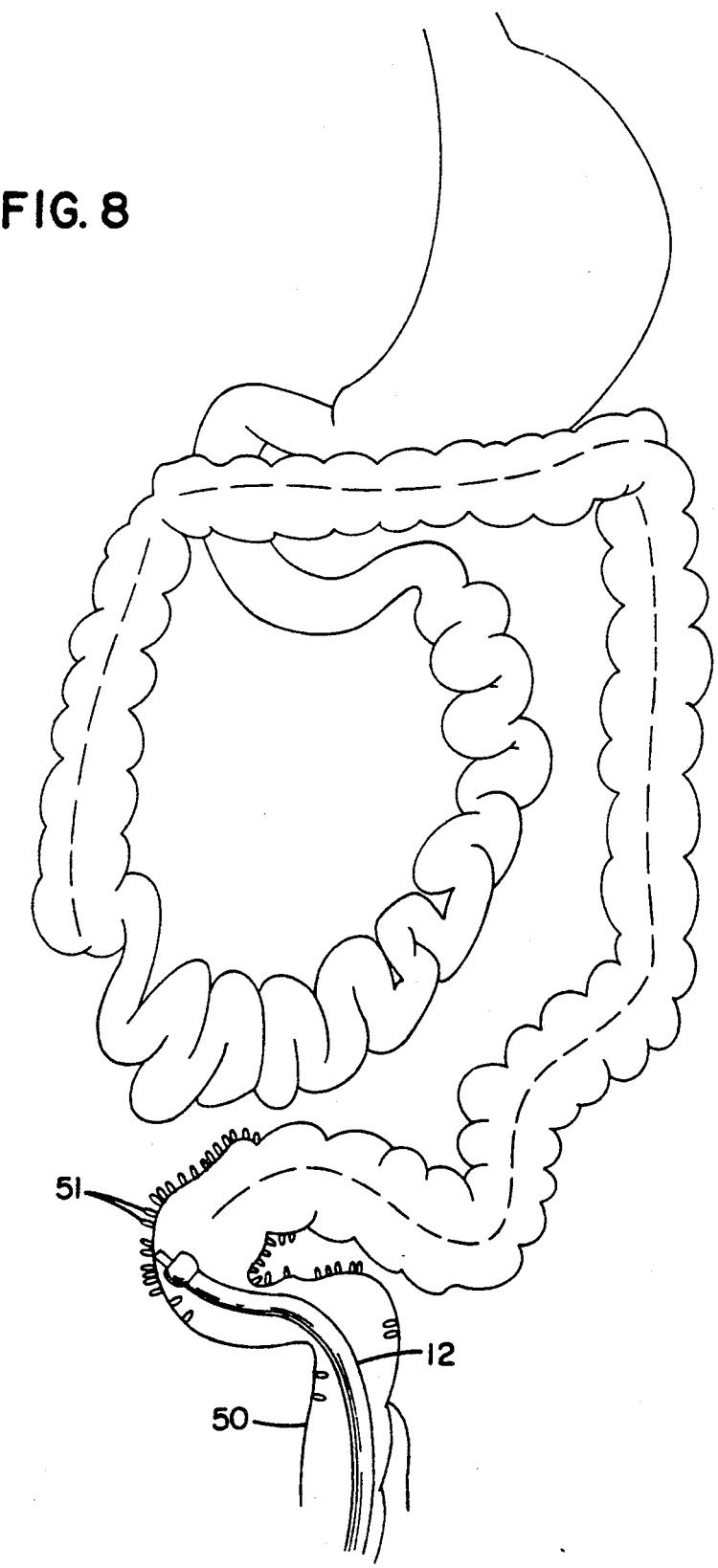

DEVICE FOR REMOVING DIVERTICULA IN THE COLON

This is a continuation of application Ser. No. 07/512,546, filed April 17, 1990, now abandoned, which is a continuation of application Ser. No. 07/215,868, filed July 6, 1988, now abandoned.

FIELD OF THE INVENTION

The present invention relates to medical devices and more particularly to a device for observing and removing diverticula from the intestine.

BACKGROUND OF THE INVENTION

About half of the population over age 50 in developed countries has diverticula which are outpouches or pockets in the colon. Such diverticula often become infected resulting in diverticulitis.

Diverticulitis is a disease in which the small pockets in the intestinal wall accumulate food residue materials which ferment, developing ballon-like pockets filled with gaseous material. The fermentation causes enlargement of the pockets, often resulting in discomfort. Sometimes the pockets rupture causing life-threatening peritonisis.

In the past, diverticulitis has been treated in various ways. The patient may be treated with drugs that minimize the fermentation reaction in the large intestine. This treatment results in some improvement, however, many pockets are closed off and thus the drugs do not readily enter the pockets. The patient may be placed on a diet which excludes food materials which are likely to cause the development of gaseous materials. For example, members of the cabbage and bean products may be eliminated from the diet.

Diagnoses of diverticulitis may be difficult. In some instances the patent is given a barium enema which coats the lining of the large intestine. X-rays are then taken and the diverticula are identified. In those instances where the pockets are closed off due to inflammation, the barium may not readily enter the pockets. In such instances, the large intestine may be injected with pressurized air which tends to enlarge the intestine, opening the pockets and permitting the barium to enter such pockets. The injection of air, of course, is a significant discomfort.

In other instances, diagnoses of diverticulitis is accomplished using a fiberoptic scope. The scope may be of the type illustrated by U.S. Pat. No. 3,643,653. Such devices include a viewing port which is connected to optic fibers running the length of a tube. The tube is inserted into the colon of the large intestine. The tube includes control mechanism that permits movement of the tube to a position adjacent the lining of the large intestine. The viewing device and the fiber optics are used to observe the lining and thereby identify the diverticula.

Upon observation of a significant diverticula problem, removal of a portion of the large intestine may be dictated. Such an operation has in the past required incision through the abdominal wall. A major surgery. Because of the seriousness of the operation, removal of diverticula sections in the past have been limited to only those cases where the diverticulitis is a very acute. Most persons having a diverticular condition have in the past been required to suffer discomfort at various periods throughout their life.

The present invention provides a device for removal of diverticula without incision. The present invention also provides a method for treating diverticula without incision through the abdominal wall.

SUMMARY OF THE PRESENT INVENTION

The present invention provides a medical device, including an elongated tube, carrying a plurality of optical fibers together with a viewing device that permits observation through the optical fibers. The tube may also include a vacuum tube for vacuumizing the diverticula to invert such diverticula. Mechanism is included for securing the diverticula in the inverted condition, thereby resulting in the adjacent external wall of the diverticula fusing e.g., growing together. This securing mechanism may be a device for placing a rubber band or a plurality of rubber bands around the diverticula. Alternatively, the mechanism may include a stapling device which staples the inverted diverticula or mechanism for securing a noose around the inverted diverticula.

The device of the present invention may be somewhat similar in structure to the Pentax Flexible Fiber Optic Sigmoid Scope, Model 35, or similar devices made by Olympus with certain modifications or improvements. Such devices have been used in the past for observation within the colon. The present invention modifies and improves such previously existing scopes to permit not only observation, but also treatment of the diverticula.

The present invention consists of a flexible tubal extension to the suction oriface of the scope. The tubal extension may include a Teflon-coated or lubricated sleeve on which is mounted either stretched small rubber bands or pre-tied nylon or biodegradable nooses or surgical staples which can be manipulated by controls attached to the scope at a location outside of the body of the patient. During use, the tubal extension is guided to the entrance of the diverticulum in the colon using the fiber optic viewer which is embedded in the flexiscope. Once in place, the scope controls may be operated to create a vacuum in the tubal extension, thereby pulling the diverticula into an inverted condition. Using the scope controls, the operator may then apply the vacuum to invert the diverticula extending such diverticula into the colon. The operator would then move the sleeve past the end of the tube, over the inverted diverticula to the colon wall. Using a special caliper, the operator may ease the rubber band, pre-tied noose or staple from the sleeve to around the base of the inwardly extending diverticula. If rubber bands are used, the stretched bands would retract, closing the end of the base of the diverticula. Over a period of several days, the tissue edges of the colon wall would grow together. The diverticula tissue would die and drop off to be excreted or removed through the lower end of the colon. If pre-tied nooses are used, the caliper would provide for slipping the noose off the sleeve. The noose would be attached to the caliper such that manipulation would draw the slip knot of the noose to close the diverticula. Again, the tissue would grow together and the diverticula would die and drop off. If surgical staples are used, a spring-loaded stapler would move a staple off the end of sleeve, closing the base of the diverticula.

The method of the present invention includes the steps of identifying enlarged problem diverticula, applying a vacuum to the diverticula in order to invert or turn such diverticula inside out. The method includes the further step of surrounding the base of the diverticula with a closure mechanism such as a rubber band or a staple. The exterior walls of the diverticula then grow together and the inverted diverticula dies and disintegrates.

IN THE DRAWINGS

FIG. 8 shows the present invention inserted into the colon.

DESCRIPTION OF THE PRESENT INVENTION

Figure 1:
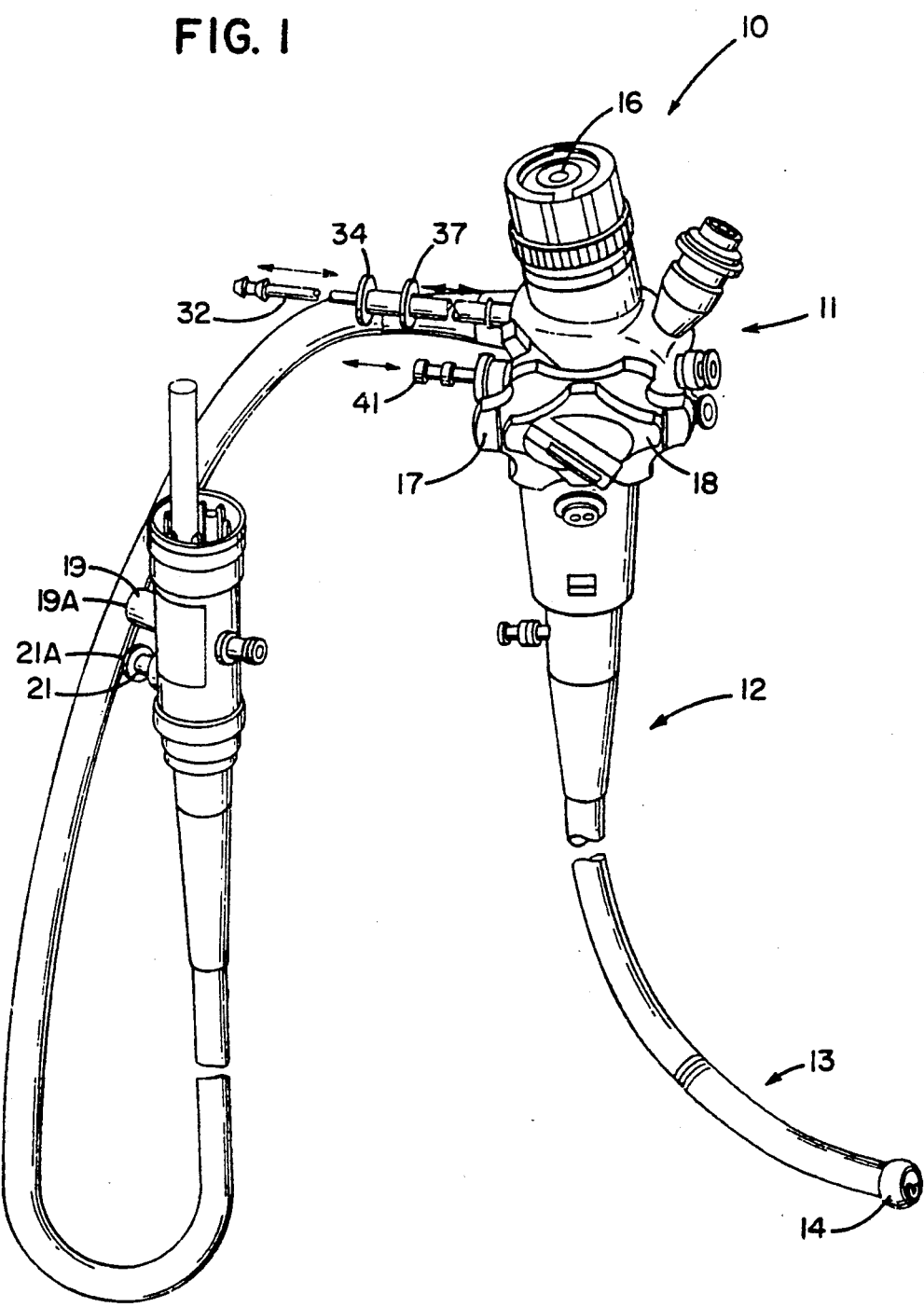
FIG. 1 is a perspective view of the device of the present invention.

The endoscopic apparatus 10 (FIGS. 1-7) of the present invention includes a control housing 11 and an elongated tube 12. The tube 12 has a bendable portion 13 adjacent to the forward end 14. The tube 12 has an image transmitting optical system commencing in the end at portion 14 and terminating in the eye piece 16 of the housing 11. In order to illuminate the object, the optical system may include a plurality of light conducting fibers which are adjacent to a plurality of optical fibers that return an image to the lens 16.

The bendable portion 13 may be controlled in a conventional manner by wires extending through the elongated tube 12. The wires may be controlled by knob 17 for movement upwardly and downwardly and by knob 18 for movement rightwardly and leftwardly. The endoscopic apparatus may include mechanism for injecting water and air through the elongated tube 12. A water channel 19 and an air channel 21 may be extended from inlets 19a and 21a along tube 12 to opening 22.

For example, a water inlet 19 and an air inlet 21 may selectively provide ejection of water and/or air through opening 22. For example for purposes of cleaning an area in the colon for observation and treatment.

The present endoscopic apparatus 10 may include mechanism 26 for inversion and tying off of the diverticula. The mechanism 26 may include a tripod-like support 27 having a ring 28 supported on legs 29, 30 and 31. The base of the legs 29, 30 and 31 may be secured to the distal end 14 of the scope. The diverticulum mechanism 26 further includes a reciprocating vacuum tube 32 which has a tapered outer end 33. Vacuum tube 32 extends along flexible tube 13 into control housing 11 and from thense out to a vacuum source. A rotatable drive 34 may be operated to reciprocate the vacuum tube 32 as will be hereinafter described.

The diverticulum mechanism 26 further includes a fastener applying to control 37. The control 37 may likewise be a rotatable mechanism for reciprocating the tube 36. Tube 36 may be tapered at its forward end and be adapted to receipt of a plurality of rubber bands such as 38. The size of the rubber bands 38 may be small enough such that they are stretched and applied over tube 36. The bands 38 tightly grip the diverticula when applied to the base of the diverticula.

Figure 7:
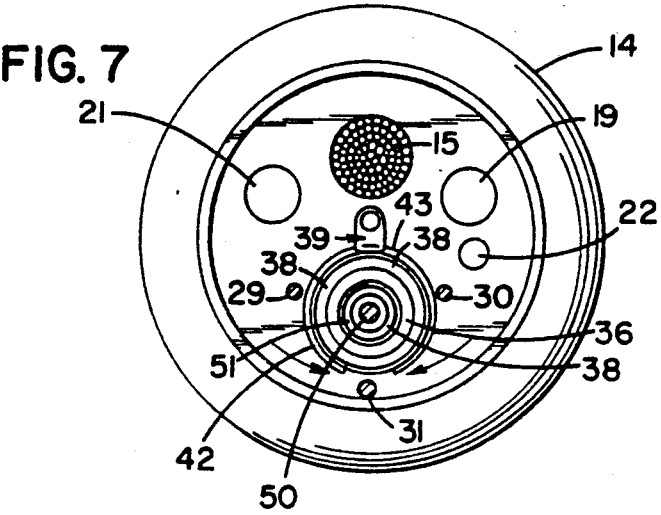

The diverticula mechanism 26 has a caliper 39 which may be reciprocated using controls 41 to maneuver one or more selected rubber bands 38 forwardly off the end of tube 36. The caliper 39, as illustrated in FIG. 7, has a first portion 42 and a second portion 43. The portions 42 and 43 may be biased toward each other and the control 41 may overcome the bias to open the caliper and permit movement along the series of rubber bands.

OPERATION OF THE PRESENT INVENTION

Figure 2:
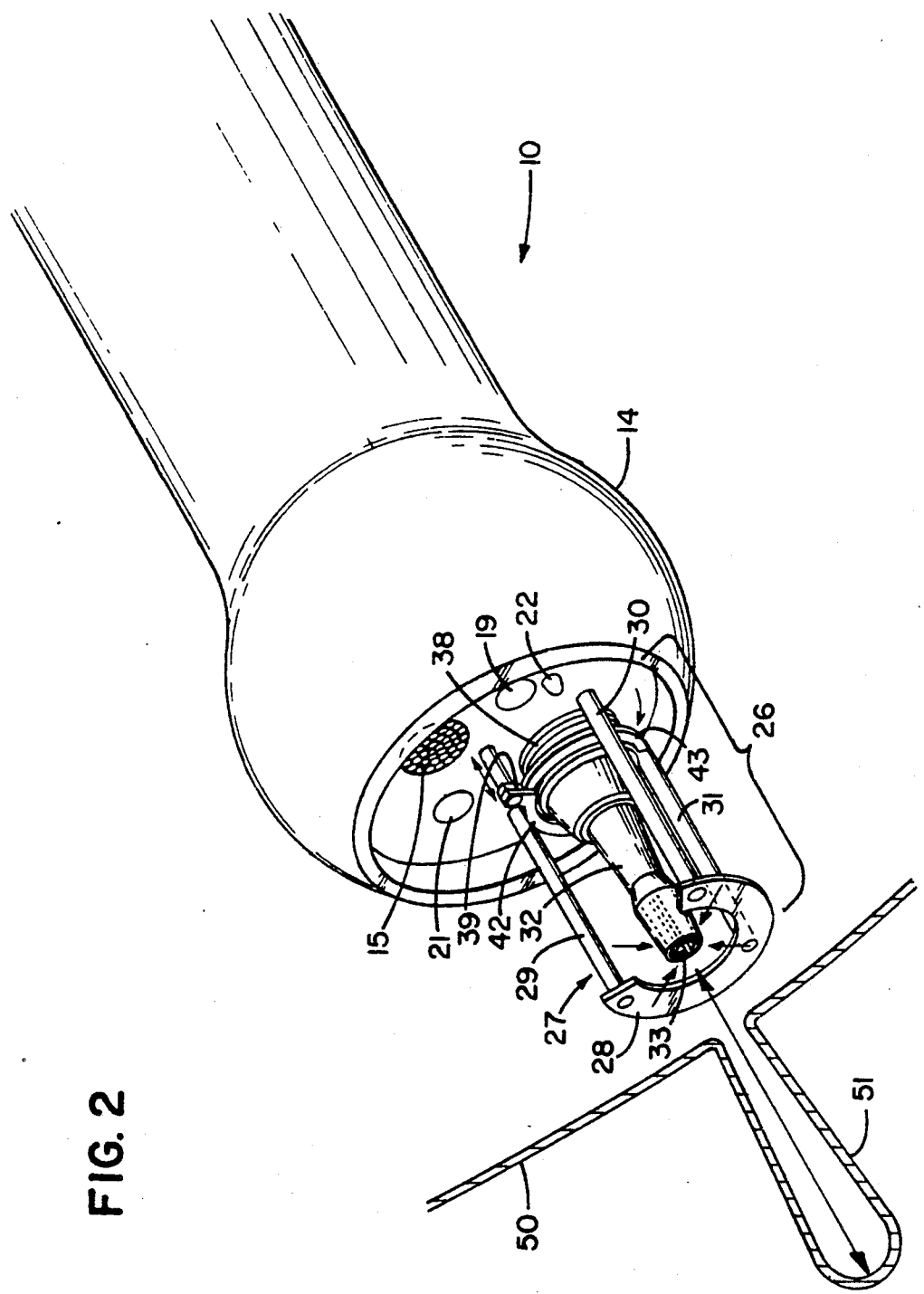
FIG. 2 is a perspective view of the forward end of the present invention.
Figure 3:
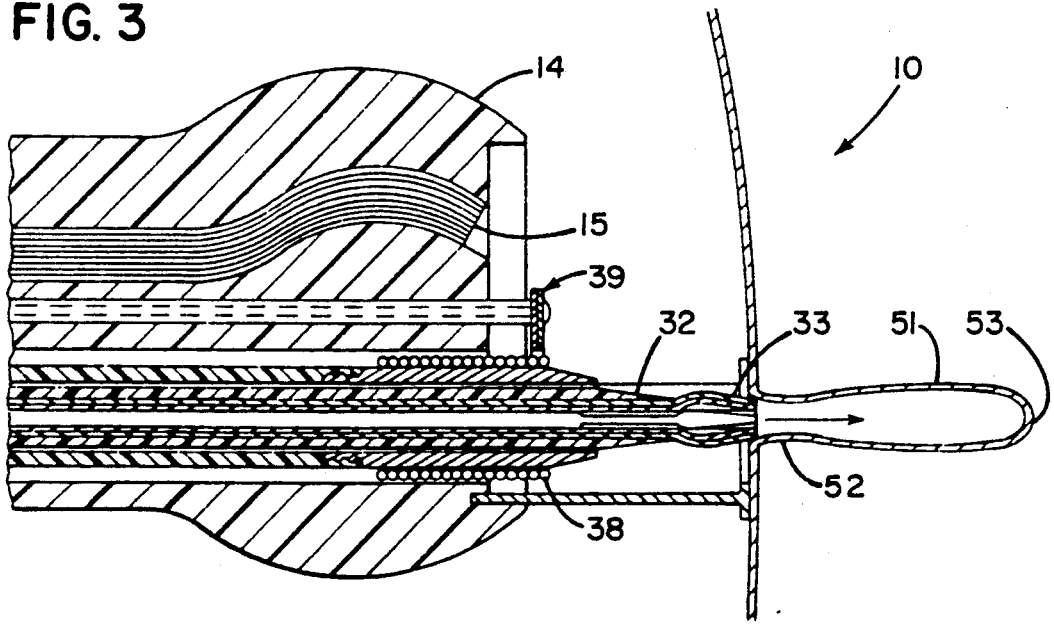
FIGS. 3 through 7 are cross-sectional views of the present invention in various operating positions.
Figure 4:
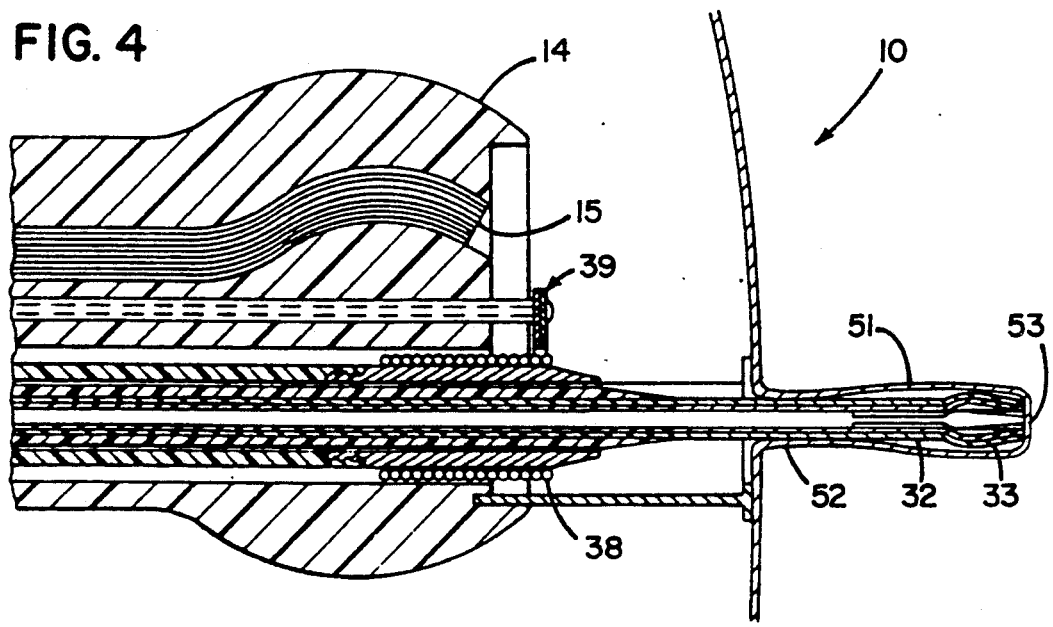
Figure 5:
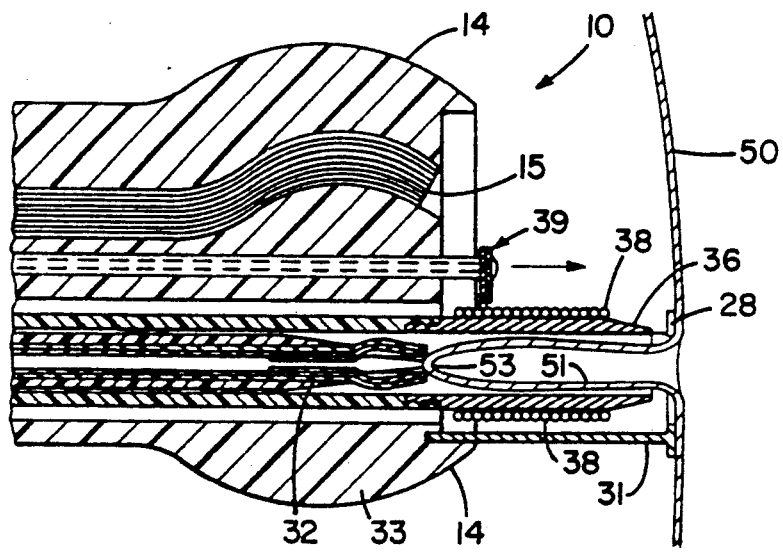
Figure 6:
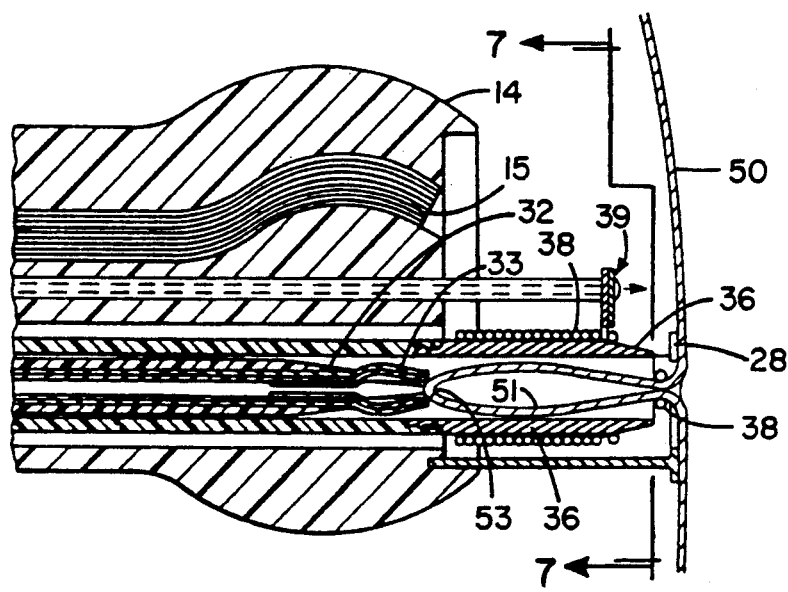

As illustrated in FIG. 8, the elongated tube 12 of the endoscopic apparatus 10 may be inserted into the patient's colon 50. The control knobs 17 and 18 may be manipulated to bring the forward end 14 of tube 12 to an appropriate diverticula 51. The diverticula 5 is an elongated pocket of finger-like in shape, as illustrated in FIG. 2. The tripod support 27 is brought into position over the diverticulum 51 by observation through the fibers 15. Some of the fibers carry light to the diverticula, while other fibers return the visual light reflection from the diverticula. It may be necessary to inject water and/or air through opening 22 to clean the site of the diverticula 51. Once the tripod support 27 is properly in place, as illustrated in FIG. 3, the vacuum tube 32 is maneuvered forwardly such that the end 33 confronts the opening 52 in the diverticula 51. The tube 32 may be further extended such that the end 33 moves into the diverticula 51 until it confronts the bottom end 53 of diverticula 51 as illustrated in FIG. 4. A vacuum is then applied through tube 32 and the tube 32 is withdrawn as shown in FIG. 5, pulling the diverticula 51 into the tube 36, completely inverting the diverticula 51. Simultaneously the tube 36 may be extended forwardly until it approaches the ring 28 of tripod support 27 as illustrated in FIG. 5. The caliper 39 is then moved forwardly until the portions 42 and 43 lie between the first and second rubber bands on tube 36. The portions 42, 43 are then rotated toward one another, thus grasping the rubber band 38 to be removed and applied to the diverticula 51 as illustrated in FIG. 6. The rubber band 38 then contracts closing the inverted diverticula 51. The tube 36 may then be withdrawn, the vacuum of tube 32 released and the elongated tube 12 moved to another site for treatment in a similar manner of another diverticula.

While a particular embodiment of the present invention is illustrated in FIGS. 1-7, various modifications may be made without departing from the broader scope of the present invention. For example, the tube 36 may alternately carry a plurality of staples which may be suitably removed by the caliper 39 and collapsed around an inverted diverticula in a manner much like that illustrated with the rubber band. Alternatively, a slip noose may be carried on the tube 36 with an end attached to the caliper 39. When the noose is inserted over the inverted diverticulum, and the caliper is withdrawn, the caliper may draw on the free end of the noose to tighten the noose down around the inverted diverticula in a manner similar to the rubber band 38.

What is claimed is:

1. An endoscopic apparatus adapted to be inserted into the colon and intestine to view and treat diverticula, said apparatus including:

an endoscope comprising a first, elongated, tubular member having longitudinally terminal front and rear parts, and a flexible part intermediate said terminal parts;

guide mechanism extending longitudinally along said flexible intermediate part to adjustably control the location of said front part with respect to said rear part;

an optical system including an objective lens means associated with said front part, an ocular means associated with said rear part and an image transmitting means associated with said intermediate part for transmitting the image received by said objective lens means to said ocular means;

a support extending from said front part terminating in a front structure, said front structure engageable with an area surrounding said diverticula;

a tubular wall member extending along said intermediate part to said front part, said tubular wall member being adapted to dilate an entrance of said diverticula and to apply a vacuum to inner tissue of said diverticula thereby inverting said diverticula, said tubular wall member including reciprocating tubular means for insertion into said diverticula to open said diverticula and apply a vacuum to said inner tissue of said diverticula and means for withdrawing said tubular means thereby inverting said diverticula, said tubular means including a slidably mounted vacuum tube having a first end with a rounded perforated tip engageable with said inner tissue of said diverticula to apply said vacuum to said inner tissue, said vacuum tube being movable to a first position for dilation of and insertion into said diverticula wherein said first end of said vacuum tube extends from said front part further than said support, said vacuum tube being movable from said first position to a second position for inverting said diverticula relative to said area surrounding said diverticula wherein said support extends from said front part further than said first end of said vacuum tube;

means associated with said tubular wall member to apply fastening means around the base of said inverted diverticula.

2. The endoscopic apparatus of claim 1 wherein said means for applying fastening means comprise means for stretching a rubber band, slipping said rubber band over diverticula and releasing said rubber band to tightly engage said diverticula at said base.

3. The endoscopic apparatus of claim 2, wherein said means for stretching a rubber band, slipping said rubber band over said diverticula, and releasing said rubber band comprises:

an outer tube mounted to said front part, said outer tube being positioned between said vacuum tube and said support, said outer tube surrounding said vacuum tube, said outer tube terminating in a tip portion, said rubber band being initially positioned in a stretched state about an outer periphery of said outer tube;

a longitudinally extendable member mounted to said front part, said extendable member having a portion engageable with said rubber band positioned on said outer tube, said longitudinally extendable member moving said rubber band in a direction away from said front part past said tip portion when said vacuum tube is in said second position and said diverticula is in a inverted state, wherein said rubber band tightly engages said diverticula at said base.

4. The endoscopic apparatus of claim 2, wherein said outer tube is slidably mounted to said front part for movement relative to said first part, said outer tube further being slidably movable relative to said vacuum tube.

5. The endoscopic apparatus of claim 3, wherein said outer tube includes a plurality of rubber bands positioned on said outer tube, and said longitudinally extendable member is mounted to said front part for reciprocal movement relative to said outer tube, said longitudinally extendable member including at least one caliper arm reciprocally movable toward and away from said outer periphery of said outer tube, said caliper arm moving toward said outer tube into engagement with a selected rubber band nearest said tip portion of said outer tube before said longitudinally extendable member extends to move said rubber band from said outer tube into engagement with said diverticula, said caliper arm moving away from said outer tube before said longitudinally extendable member is completely retracted toward said front part.

6. An endoscopic apparatus adapted to be inserted into the colon to view and treat tissue, said apparatus including:

an endoscope comprising a first, elongated, tubular member having longitudinally terminal front and rear parts, and a flexible part intermediate said terminal parts;

a guide mechanism extending longitudinally along said flexible intermediate part to adjustably control the location of said front part with respect to said rear part;

an optical system including an objective lens means associated with said front part, an ocular means associated with said rear part and an image transmitting means associated with said intermediate part for transmitting the image received by said objective lens means to said ocular means;

an outer tube extending from said front part, said outer tube terminating in a tip portion, said outer tube having an outer periphery, said tip portion being positionable around a portion of tissue extending into said colon, said outer tube being slidably mounted to said front part of said endoscope for movement relative to said front part;

a plurality of rubber bands, each rubber band positioned in a stretched state about said outer periphery of said outer tube; and a longitudinally extendable member mounted to said front part for reciprocal movement between an extended position and a retracted position, said extendable member having means for engaging a selected rubber band nearest said tip portion of said outer tube, wherein said rubber band is moved away from said front part past said tip portion of said outer tube and into engagement around said portion of said tissue as said extendable member moves from said retracted position to said extended position, said extendable member being retractable to said retracted position wherein said means for engaging a selected rubber band is positioned to engage the next rubber band positioned nearest said tip portion of said outer tube, and wherein said means for engaging a selected rubber band includes at least one caliper arm extending from said extendable member, said caliper arm being reciprocally movable toward and away from said outer periphery of said outer tube, said caliper arm including control means for selectively controlling movement of said caliper arm separate from movement of said longitudinally extendable member between said retraced and said extended positions.

7. The endoscopic apparatus of claim 6, further comprising means for holding said portion of tissue relative to said front part for viewing and treatment.

8. The endoscopic apparatus of claims 7, wherein said means for holding includes a vacuum tube extending from said front part adapted to apply a vacuum to at least a part of said portion of tissue to hold said portion of tissue for viewing and treatment.

9. The endoscopic apparatus of claim 6, wherein said means for engaging includes two opposing caliper arms positioned on opposite sides of said outer tube.

10. An endoscopic apparatus adapted to be inserted into the colon and intestine to view and treat tissue protruding into the colon or into the intestine, said apparatus including:

an endoscope comprising a first, elongated, tubular member having longitudinally terminal front and rear parts, and a flexible part intermediate said terminal parts;

a guide mechanism extending longitudinally along said flexible intermediate part to adjustably control the location of said front part with respect to said rear part;

an optical system including an objective lens means associated with said front part, an ocular means associated with said rear part and an image transmitting means associated with said intermediate part for transmitting the image received by said objective lens means to said ocular means;

a support extending from said front part terminating in a front structure, said front structure engageable with an area surrounding said tissue protrusion;

a tubular wall member extending along said intermediate part to said front part, said tubular wall member being adapted to apply a vacuum to an end of said tissue protrusion to hold said tissue protrusion for viewing and treatment, said tubular member including a slidably mounted vacuum tube having a first end with a tip engageable with said end of said tissue to apply said vacuum to said end of said tissue; and means associated with said tubular wall member for applying fastening means around a base portion of said tissue protrusion, said means for applying a fastening means including an outer tube mounted to said front part, said outer tube surrounding said vacuum tube, said outer tube terminating in a tip portion, said outer tube being slidably mounted to said front part for movement relative to said front part, said outer tube further being slidably moveable relative to said vacuum tube, a rubber band initially positioned in a stretched about an outer periphery of said outer tube, and a longitudinally extendable member mounted to said front part, said extendable member having a portion engageable with said rubber band positioned on said outer tube, said longitudinally extendable member moving said rubber band in a direction away from said front part past said tip portion of said outer tube wherein said rubber band tightly engages said tissue protrusion at said base portion.

* * * * *

UNITED STATES PATENT AND TRADEMARK OFFICE
CERTIFICATE OF CORRECTION

PATENT NO. : 5,100,419

DATED : March 31, 1992

INVENTOR(S) : Robert L. Ehlers

It is certified that error appears in the above-identified patent and that said Letters Patent is hereby corrected as shown below:

```
     On the title page, Item [76]: delete
     "31," before "West".
Column 1, line 65
     DELETE "a" after the word "is".

Column 2, line 64
     INSERT --the-- after the word "of".

Column 3, line 36
     DELETE "2'a" and INSERT therefor --21a--.

Column 3, line 55
     DELETE "to" after the word "applying".

Column 4, line 9
     DELETE "5" and INSERT therefor --51--.
 column 6:
Claim 8, line 1
     DELETE "claims" and INSERT therefor --claim--
```

UNITED STATES PATENT AND TRADEMARK OFFICE
CERTIFICATE OF CORRECTION

PATENT NO. : 5,100,419

DATED : March 31, 1992

INVENTOR(S) : Robert L. Ehlers

It is certified that error appears in the above-identified patent and that said Letters Patent is hereby corrected as shown below:

Column 8, Claim 10, line 18
    INSERT —state— after the word "stretched".

Signed and Sealed this

Twenty-third Day of November, 1993

Attest:

BRUCE LEHMAN

Attesting Officer     Commissioner of Patents and Trademarks